United States Patent [19]

Müller et al.

[11] Patent Number: 4,764,581

[45] Date of Patent: Aug. 16, 1988

[54] LIQUID-CRYSTALLINE DIGLYCIDYL COMPOUNDS, THE PREPARATION OF THESE, AND THE USE OF THESE IN CURABLE EPOXIDE MIXTURES

[75] Inventors: Hanns P. Müller, Odenthal; Roland Gipp, Cologne; Heinrich Heine, Leverkusen, all of Fed. Rep. of Germany

[73] Assignee: Bayer Aktiengesellschaft, Leverkusen, Fed. Rep. of Germany

[21] Appl. No.: 64,745

[22] Filed: Jun. 22, 1987

[30] Foreign Application Priority Data

Jul. 5, 1986 [DE] Fed. Rep. of Germany ....... 3622610

[51] Int. Cl.$^4$ ..................... C08G 59/24; C07D 303/16
[52] U.S. Cl. ................................. 528/100; 528/103; 549/517; 549/557
[58] Field of Search ................ 549/557, 517; 528/100

[56] References Cited

U.S. PATENT DOCUMENTS

| | | | |
|---|---|---|---|
| 2,945,426 | 2/1960 | Schroeder | 549/557 X |
| 3,073,804 | 1/1963 | Raecke et al. | 549/557 X |
| 3,477,990 | 11/1969 | Dante et al. | 528/100 X |
| 4,130,549 | 12/1978 | Ueno et al. | 528/100 X |
| 4,560,732 | 12/1985 | Kojo et al. | 528/100 X |

*Primary Examiner*—Earl Nielsen
*Attorney, Agent, or Firm*—Connolly & Hutz

[57] ABSTRACT

The invention relates to new, liquid-crystalline diglycidyle compounds of optionally ring-substituted 4-hydroxyphenyl 4-hydroxybenzoates, a synthesis of p-epoxypropoxy-phenyl p-epoxy-propoxybenzoate, furthermore epoxy resin mixtures containing the new diglycidyle compounds, and the use of the new diglycidyl compounds and the epoxy resin mixtures thereof in curable mixtures.

5 Claims, No Drawings

LIQUID-CRYSTALLINE DIGLYCIDYL COMPOUNDS, THE PREPARATION OF THESE, AND THE USE OF THESE IN CURABLE EPOXIDE MIXTURES

The invention relates to new, liquid-crystalline diglycidyl compounds of optionally ring-substituted 4-hydroxyphenyl 4-hydroxybenzoates, a synthesis of p-epoxypropoxy-phenyl p-epoxy-propoxy benzoate, furthermore epoxy resin mixtures containing the new diglycidyl compounds, and the use of the new diglycidyl compounds and the epoxy resin mixtures thereof in curable mixtures. tures.

Amongst the industrially customary epoxy resins, the diglycidyl ethers of "bisphenol A" has the greatest importance. The properties of the cured resins are very strongly influenced by the structure of the reactants, that is to say the diglycidyl ethers, and the type of accelerator.

Diglycidyl compounds of optionally ring-substituted 4-hydroxy-phenyl 4-hydroxybenzoates were hitherto not known.

It has been shown that these compounds have a liquid-crystalline character and thus make possible the construction of epoxy resins having particular physical properties.

Surprisingly, it has also been found that these diglycidyl compounds of optionally ring-substituted 4-hydroxy-phenyl 4-hydroxybenzoates can be obtained in good yields when the synthesis is carried out in a fashion known per se in the presence of sodium hydroxide with excess epichlorohydrin. This fact is surprising since those skilled in the art would have expected aryl benzoates to be hydrolytically cleaved under the reaction conditions used. Surprisingly, this is hardly the case, i.e. only to a very minor extent.

The invention therefore relates to diglycidyl compounds of the formula (I)

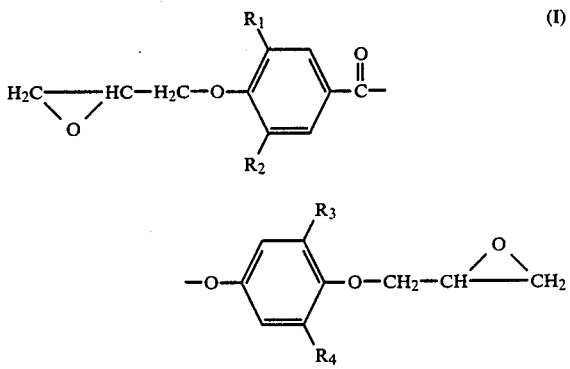

in which $R_1$, $R_2$, $R_3$ and $R_4$, independently of one another denote hydrogen, halogen or alkyl having 1 to 6 C atoms, preferably 1 to 4 C atoms.

The invention also relates to a process for the preparation of the diglycidyl compounds of the formula (I), characterized in that optionally ring-substituted 4-hydroxyphenyl 4-hydroxybenzoates (II) are reacted, in a fashion known per se, with excess epichlorohydrin in the presence of catalysts and alkali metal compounds.

The present invention finally relates to (curable) mixtures containing diglycidyl compounds of the formula (I), if appropriate as blends with di-, tri- and tetraglycidyl compounds which are known per se (and curing agents for epoxy resins).

The mixtures preferably contain at least 5 % by weight of (I), preferably at least 20 % by weight of (I).

The compounds of the formula (I) according to the invention can be prepared by glycidylating a bisphenol of the formula (II).

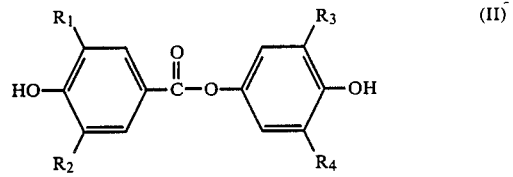

in which $R_1$, $R_2$, $R_3$ and $R_4$ have the same meaning as in formula (I), by means of an epihalogenohydrin to form a compound of the formula (I).

The glycidylation of organic compounds having hydroxyl groups represents a type of reaction which is known in principle. For example, bisphenols of the formula (II) can be reacted with epichlorohydrin to form a dichlorohydrin of the formula (III), which is then dehydrochlorinated.

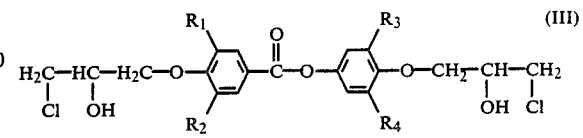

The following method is preferably used: In a 2-stage process, 1 mole of bisphenol is initially treated with at least 10 moles, preferably 20 to 40 moles, of epichlorohydrin in the presence of a catalyst (for example tetraalkylammonium chloride), a dichlorohydrin of the formula (III) being produced. In the equilibrium, glycid ether and 1,3-dychloroisopropanol form during the reaction due to the reaction of 3-chloro-2-hydroxypropyl ether groups with epichlorohydrin. In the second stage, the bischlorohydrin ether (III) is treated with alkali, the epoxide groups being formed and the 1,3-dichloroisopropanol present being reconverted into epichlorohydrin.

The alkali is normally sodium hydroxide, but other alkaline substances, such as barium hydroxide or potassium carbonate, may alternatively be used for the conversion of the 1,2-chlorohydrin groups into 1,2-epoxide groups.

The reaction may also be carried out in a solvent, for example hydrocarbons, ethers or ketones, but an excess of epichlorohydrin is preferably used as solvent. The reaction is generally carried out at elevated temperature, such as at 40° to 100° C.

As compounds of the formula (II), those are preferably used in which $R_1$, $R_2$, $R_3$ and $R_4$, independently of one another, denote hydrogen, chlorine, bromine or alkyl having 1 to 4 C atoms; the compound I having $R_1$, $R_2$, $R_3$ and $R_4$=hydrogen is particularly preferred.

The synthesis of the bisphenol of formula (II) in which $R_1$, $R_2$, $R_3$ and $R_4$ each denote a hydrogen atom is claimed in German Patent Application No. P 36 22 611.

The mixtures, according to the invention, of epoxy resins with di-, tri- and tetraglycidyl compounds, known per se, are preferably prepared by simple mixing of a diglycidyl compound of the formula (I) with known epoxy resins, as described, for example, in Polymere Werkstoffe [polymeric materials], volume III, Technologie 2 [Technology 2], published by H. Batzer, page 171 to 174, Georg Thieme Verlag, Stuttgart/New York, 1984.

Another way of preparing the epoxy-resin mixtures according to the invention comprises glycidylating a mixture of bisphenols of the formula (II) and, for example, bisphenol A, aromatic diamines, aminophenols or heterocyclic compounds, such as, for example, cyanuric acid.

The diglycidyl compounds according to the invention, and the mixtures thereof with known epoxy resins, can be cured with the curing agents which are conventional for epoxy resins.

Examples of curing agents which may be mentioned are the customary curing agents for epoxy resins, including aliphatic, cycloaliphatic, aromatic and heterocyclic amines, such as bis-(4-aminophenyl)-methane, anilineformaldehyde resin, bis-(4-aminophenyl) sulfone, propane-1,3-diamine, hexamethylenediamine, diethylenetriamine, triethylenetetraamine, 2,2,4-trimethylhexane-1,6-diamine, m-xylylenediamine, bis-(4-aminocyclohexyl) methane, 2,2-bis-(4-aminocyclohexyl)-propane and 3-aminomethyl-3,5,5-trimethylcyclohexylamine (isophoronediamine), polyaminoamides, such as, for example, those made from aliphatic polyamines and dimerized or trimerized fatty acids, polyphenols, such as resorcinol, hydroquinone, 2,2-bis(4-hydroxyphenyl)-propane and phenol-aldehyde resins, polythiol, such as the polythiols which are commercially available under the name "Thiokols", polycarboxylic acids and the anhydrides thereof, such as, for example, phthalic anhydrids, tetrahydrophthalic anhydride hexahydrophthalic anhydride, hexachloroendomethylenetetrahydrophthalic anhydride, pyromellitic anhydride, benzophenone-3,3′, 4,4′-tetracarboxylic dianhydride, the acids of the abovementioned anhydrides, and also isophthalic acid and terphthalic acid. Catalytically active curing agents, for example tertiary amines [for example 2,4,6-tris-(dimethylaminoethyl)-phenol)], imidazoles and other Mannich bases; alkali metal alkoxides of alcohols (for example Na alcoholate of 2,4-dihydroxy-3-hydroxymethyl-pentane), tin salts of alkanoic acids (for example tin octanoate), Friedel-Crafts catalysts, such as boron trifluoride and boron trichloride, and the complexes and chelates thereof which are obtained by reacting boron trifluoride with, for example, 1,3-diketones.

With the curing agents, suitable curing accelerators can also be employed. When using poly-(aminoamides), polythiols or polycarboxylic acid anhydrides, tertiary amines or the salts thereof, quaternary ammonium compounds or alkali metal alkoxides can serve as accelerators.

The amount of the curing agent employed depends on the chemical nature of the curing agent and on the desired properties of the curable mixture and the cured product. The maximum amount can easily be determined. When the curing agent is an amine, 0.75 to 1.25 equivalents of amine-hydrogen are normally employed per equivalent of epoxide. When polycarboxylic acids or the anhydrides thereof are employed, 0.4 to 1.1 equivalents of carboxyl group or anhydride group are usually used per equivalent of epoxide group. When using polyphenols as curing agents, 0.75 to 1.25 phenolic hydroxyl groups are expediently employed per epoxide equivalent.

Catalytically active curing agents are generally employed in amounts from 1 to 40 parts by weight per 100th part by weight of epoxy resin.

Depending on the nature of the curing agent used, the curing can be carried out at room temperature or at elevated temperatures. If desired, the curing can alternatively be carried out in 2 steps, for example by interrupting the curing process or, if using a curing agent for elevated temperatures, allowing the curable mixture to partially cure at lower temperatures. The products obtained in this curing procedure are still meltable and soluble precondensates (so-called "B-step resins") and are suitable, for example, for molding materials, sintering powders or prepregs.

The curable mixtures according to the invention can furthermore contain plasticizers, such as dibutylphthalate, dioctyl phthalate or tricresyl phosphate, or additives, such as extenders, fillers, reinforcing agents, colorants, flow agents and mold-release agents. Suitable extenders, fillers and reinforcing agents are, for example, asbestos, asphalt, bitumen, glass fibers, textile fibers, carbon or boron fibers, mica, alumina, plaster, titanium dioxide, chalk, quartz sand, cellulose, kaolin, ground dolomite, wollastonite, silica with a large surface area (available under the trade name "Aerosil ®"), alumina which is modified with long-chain amines (available under the trade name "Bentone ®"), powdered polyvinyl chloride, polyolefin or aminoplastic resins and metal powders, such as aluminium or iron powder. Flameproofing agents, such as antimony trioxide, can likewise be added to the curable mixtures.

The curable materials according to the invention can be used, for example, as laminating resins, impregnating resins and casting resins, powder coatings, molding materials, cements and sealants, embedding materials and insulating materials for electrotechnology, and, in particular, as adhesives or matrix resins for the preparation of fiber-reinforced plastics.

EXAMPLES

EXAMPLE 1

Preparation of p-epoxy-propoxyphenyl p-epoxypropoxybenzoate (I)

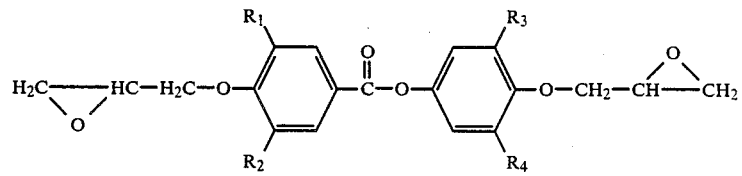

Batch:
2275 g (30 mol) of epichlorohydrin
4 g of tetraethylammonium chloride
230 g (1 mol) of 4-hydroxyphenyl 4-hydroxy benzoate (II)

222 g (2.5 mol) of 45 % strength NaOH

The epichlorohydrin, the 4-hydroxyphenyl 4-hydroxybenzoate (II) and the tetraethylammonium chloride are reacted for 16 hours at 60° C. under N₂ in a 4 litre 3-neck flask which is equipped with internal thermometer, stirrer and—via a water separator—a reflux condenser. The subsequent dehydrohalogenation is carried out within 6 hours at 130 mbar and 60° C. by continuous dropwise addition of aqueous NaOH. In this reaction, the water is removed continuously via the water separator.

When the NaOH addition is complete, the mixture is stirred for a further 3 hours under the same conditions. The sodium chloride is subsequently filtered off and washed with fresh epichlorohydrin, and the combined filtrates are concentrated at 13 mbar and a bath temperature of 50° C. The epichlorohydrin removed by distillation is reused for the next batch. The residue is dissolved in 200 ml of acetonitrile and, after addition of 1 litre of methanol, brought to crystallization. The crystals are filtered off under suction, washed with methanol and dried in vacuo over silica gel at room temperature.

Yield: 242 g (71% of theory)

Melting point: 105°–107° C. After recrystallizing twice from acetonitrile/isopropanol (1:1), the melting point increases to 118° C.

Melting point: 118° C. (differential thermoanalysis)

p-Epoxypropoxyphenyl p-epoxypropoxybenzoate has a liquid-crystalline character:

Quantitative DTA (differential thermoanalysis) and polarized-light microscopic measurements show that, on cooling from the melt, the compound changes into the nematic state at 93° C. and into the solid state at 80° C.

DTA measurement, Mettler TA 2000 instrument, quantitative measurement cells, aluminium crucible, preliminary measurement: 2 K/min.

Polarized-light microscopic measurement: Mettler FP 6 instrument, 60x magnification, crossed polarizing filters.

Specific curing reactions utilizing the liquidcrystalline behaviour of p-epoxy-propoxyphenyl p-epoxypropoxybenzoate (I) are described in German Patent Application P 36 22 613.

EXAMPLE 2

100 parts by weight of p-epoxypropoxyphenyl p-epoxypropoxybenzoate (I) from Example 1 are warmed to 80° C. with 90 parts by weight of hexahydrophthalic anhydride and 1.9 parts by weight of dimethylbenzylamine. During this warming, a liquid, homogeneous mixture is produced. The mixture is cast in a mould (200 mm x 300 mm x 4 mm) for 4 hours at 80° C., then cured at 120° C. for 16 hours. Test samples are cut from the moulded element obtained and the mechanical properties thereof are determined.

Tensile strength (MPa): 65
Elongation at tear (%): 3.2
E modulus from tensile test (MPa): 3070
Flectional strength (MPa): 122
Edge fibre elongation (%): 5.7
Toughness (kJ/m²): 20.5
Ball indentation hardness (MPa): 164
Martens temperature (°C.): 128

The gelling time at 160° C. is 40 seconds.

EXAMPLE 3

90 parts by weight of the diglycidyl ether of bisphenol A having a viscosity of 15,000 mPa.s/25° C. and an epoxide equivalent of 195 are mixed with 10 parts by weight of p-epoxypropoxyphenyl p-epoxypropoxybenzoate from Example 1. A clear solution is produced by heating to 120° C. The solution is then cooled to room temperature. In this fashion, a usable, clear epoxy resin mixture, which has a viscosity of 15,300 mPa.s/25° C. and which can be cured cold and hot by conventional processes, is produced.

We claim:

1. Liquid-crystalline diglycidyl compounds of the formula (1)

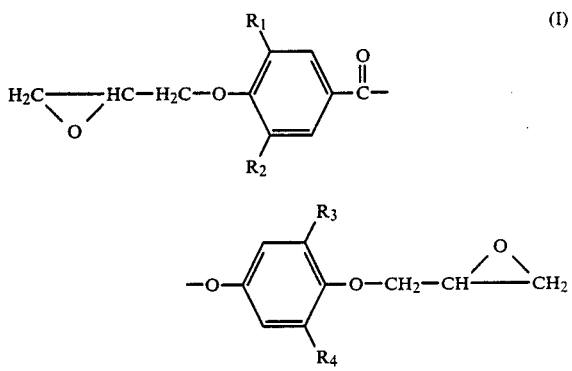

in which R₁, R₂, R₃ and R₄, independently of one another, denote hydrogen, halogen or alkyl having 1 to 6 C atoms.

2. Diglycidyl compounds according to claim 1, characterized in that R₁, R₂, R₃ and R₄ is hydrogen.

3. Process for the preparation of diglycidyl compounds of the formula (I) corresponding to claim 1, characterized in that 4-hydroxyphenyl 4-hydroxybenzoates or ring substituted 4-hydroxyphenyl 4-hydroxybenzoates are reacted, with epichlorohydrin in the presence of catalysts and alkali metal compounds.

4. Curable mixtures, containing diglycidyl compounds of the formula (I) according to claim 1, optionally blended with di-, tri-, and tetraglycidyl compounds and a curing agent for epoxy resins.

5. The process of claim 3 wherein the alkali metal compound is sodium hydroxide.

* * * * *